US007196051B2

(12) United States Patent
Kuhn et al.

(10) Patent No.: US 7,196,051 B2
(45) Date of Patent: Mar. 27, 2007

(54) PROCESS FOR THE PREPARATION OF CYCLOHEXYLOXYACETIC ALKYL ESTERS

(75) Inventors: Walter Kuhn, Holzminden (DE); Hans-Ulrich Funk, Lauenförde (DE); Gerhard Senft, Holzminden (DE)

(73) Assignee: Symrise GmbH & Co. KG, Holzminden (DE)

( * ) Notice: Subject to any disclaimer, the term of this patent is extended or adjusted under 35 U.S.C. 154(b) by 225 days.

(21) Appl. No.: 10/308,951

(22) Filed: Dec. 3, 2002

(65) Prior Publication Data

US 2003/0109415 A1    Jun. 12, 2003

(30) Foreign Application Priority Data

Dec. 6, 2001    (DE)    ................ 101 60 008

(51) Int. Cl.
*A61K 8/18*    (2006.01)
(52) U.S. Cl. ....................... 512/25; 560/126
(58) Field of Classification Search .................. 512/25; 560/126
See application file for complete search history.

(56) References Cited

U.S. PATENT DOCUMENTS

| 3,780,087 A | 12/1973 | Keine |
| 3,806,539 A | 4/1974 | Keine |
| 4,196,303 A * | 4/1980 | Kane et al. ............... 560/126 |
| 4,504,412 A | 3/1985 | Harris |
| 6,399,810 B1 | 6/2002 | Kuhn et al. |

FOREIGN PATENT DOCUMENTS

| DE | 197 55 598 | | 6/1999 |
| EP | 1 078 912 A2 | | 8/2002 |
| JP | 407238297 | * | 9/1995 |
| PL | 150119 | * | 4/1990 |
| WO | WO 9918926 | | 4/1999 |

OTHER PUBLICATIONS

Perfumer & Flavorist, vol. 25, Jan./Feb. 2000, pp. 19-23, Libor Červeny, Martina Pustêjovaká and Petr Kačer, "The Snythesis of Allyl-3-Cyclohexylpropionate".
Bull. Soc. Chim.Fr., (month unavailable) 1928, 4, p. 903, L. Falfray et al.
Chem. Ber., 93, (month unavailable) 1960, pp. 1129-1137, Gerhard Hesse und Suresh Majmudar, "Ester der schwefligen und selenigen Säure".

* cited by examiner

*Primary Examiner*—Monique T. Cole
(74) *Attorney, Agent, or Firm*—Akerman & Senterfitt; Stephan A. Pendorf

(57) ABSTRACT

The invention relates to a process for the preparation of cyclohexyloxyacetic alkyl esters by hydrogenation of phenoxyacetic alkyl esters and to the use of cyclohexyloxyacetic alkyl esters as fragrances.

9 Claims, No Drawings

PROCESS FOR THE PREPARATION OF CYCLOHEXYLOXYACETIC ALKYL ESTERS

FIELD OF THE INVENTION

The invention relates to a process for the preparation of cyclohexyloxyacetic alkyl esters by hydrogenation of phenoxyacetic alkyl esters and to the use of cyclohexyloxyacetic alkyl esters as fragrances.

BACKGROUND OF THE INVENTION

Cyclohexyloxyacetic alkyl esters can be used as starting materials for the preparation of fragrances. For example, methyl cyclohexyloxyacetate is used as starting material for the preparation of allyl cyclohexyloxyacetate, as described, for example, in Perfumer & Flavorist, Vol. 25, Jan.–Feb. 19, 2000.

Allyl cyclohexyloxyacetate is a colorless liquid with a fruity, pineapple-like odour and is available commercially under the name Isoananat (Manufacturer: Haarmann & Reimer GmbH).

Bull. Soc. Chim. Fr. 1928, 4, 903 describes the preparation of methyl cyclohexyloxyacetate by hydrolysis of cyclohexyloxyacetonitrile by means of methanolic hydrogen chloride solution without giving the yield.

In Chem. Ber. 1960, 93, 1129, ethyl cyclohexyloxyacetate is prepared by reaction of cyclohexanol and ethyl diazoacetate with 26% yield.

The processes mentioned are unsatisfactory because of the starting materials, which can only be prepared in a complex manner, and also with regard to the yield.

An object of the present invention was to find a process which permits the preparation of cyclohexyloxyacetic alkyl esters in good yield.

SUMMARY OF THE INVENTION

The invention relates to a process for the preparation of cyclohexyloxyacetic alkyl esters by hydrogenation of phenoxyacetic alkyl esters in the presence of a catalyst containing at least one metal from subgroup 8 in elemental form.

The present invention further provides for the use of cyclohexyloxyacetic alkyl esters having alkyl radicals containing 1 to 12 carbon atoms as fragrances.

DETAILED DESCRIPTION OF THE INVENTION

The process according to the invention can be represented by the following reaction equation:

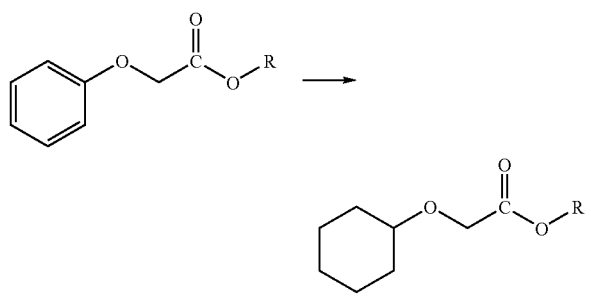

Suitable alkyl radicals R contain 1 to 12 carbon atoms. Preferred alkyl radicals R are unbranched, branched or cyclic $C_1$–$C_8$-alkyl radicals, and R is particularly preferably methyl, ethyl, propyl, isopropyl, butyl, isobutyl, tertiary butyl, pentyl, isopentyl, hexyl, isohexyl, heptyl, isoheptyl, octyl, isooctyl, cyclopentyl, cyclohexyl, cycloheptyl, methylcyclopentyl, methylcyclohexyl, methylcycloheptyl, dimethylcyclopentyl, dimethylcyclohexyl, ethylcyclopentyl and ethylcyclohexyl, and R is very particularly preferably methyl, ethyl, propyl, isopropyl, butyl, isobutyl and tertiary butyl.

Phenoxyacetic alkyl esters are easily accessible by reacting phenol and chloroacetic alkyl esters, as described, for example, in DE-A 19755598.

According to the present invention, catalysts are to be understood as meaning products which have a catalytic action in the hydrogenation in the process according to the present invention.

The catalysts according to the present invention comprise at least one metal from subgroup 8 in elemental, metallic form.

These metals can, for example, be used in finely divided form, applied to supports or together with other metals (e.g. mixtures, alloys). The catalysts can comprise dopings with one or more arbitrary metals.

Suitable catalysts can comprise, for example, ruthenium, rhodium, iridium, nickel, palladium or platinum. Advantageous catalysts for the purposes of the process according to the present invention comprise palladium, platinum, ruthenium or rhodium. A more preferred catalyst comprises palladium.

The metals according to the present invention can be applied to organic or inorganic support materials. The catalysts can comprise a support material or mixtures of support materials. Advantageous support materials which may be mentioned are: activated carbon, carbon, aluminum oxides, metal oxides, silica gels, zeolites, clays, clay granules, amorphous aluminum silicates and other inorganic supports. A preferred support material is activated carbon.

A more preferred catalyst is palladium on activated carbon.

In the process according to the present invention, the catalyst is used in amounts for which the weight ratio of the amount of metal to phenoxyacetic alkyl ester is in the range from 1:100 to 1:10 000, preferably in the range from 1:500 to 1:5 000, more preferably in the range from 1:1,000 to 1:3,000.

The amount of metal herein refers to the absolute content of the metal of subgroup 8 or the total content of metals of subgroup 8, i.e. without support material and without water or diluents which may be present.

If catalysts comprising support materials are used, the proportion of metal on the support material may generally be 0.5 to 50% by weight, preferably 1 to 20% by weight, more preferably 3 to 10% by weight, based on the dry catalyst.

For the process according to the present invention, the catalyst can be used in the dry or moist state (residual moisture of water).

The process can be carried out continuously, semicontinuously and batchwise.

The process according to the present invention can be carried out using solvents or solvent mixtures. Suitable are, for example, alcohols, aqueous alcohols, ethers, esters, aromatic or saturated hydrocarbons. For example, solvents such as methanol, ethanol, isopropanol, n-propanol, isobutanol, n-butanol, sec-butanol, tetrahydrofuran, dibutyl ether, ethylene glycol dimethyl ether, ethyl acetate, methyl acetate, pentane, hexane, heptane, octane, cyclopentane, cyclohexane, methylcyclohexane, cyclooctane, benzene, toluene, ethylbenzene or xylenes can be used.

The process is preferably carried out without a solvent.

The hydrogenation can be carried out at temperatures in the range from 50 to 200° C., preferably in the range from 70 to 160° C., more preferably at 90 to 130° C.

According to the present invention, the hydrogenations are carried out with elemental hydrogen.

The hydrogen pressure is suitably 1 to 100 bar, preferably 10 to 30 bar.

The reaction time is preferably 1 to 100 hours, more preferably 10 to 50 hours, and most preferably 20 to 40 hours.

The process according to the present invention is generally carried out as follows.

Phenoxyacetic alkyl ester and the catalyst and optionally, a solvent are initially introduced into a pressure vessel with stirrer. Hydrogenation is carried out at the chosen reaction temperature and hydrogen pressure. The resulting cyclohexyloxyacetic alkyl ester is obtained following removal of the catalyst by filtration, decantation or centrifugation. If necessary, the cyclohexyloxyacetic alkyl ester can be purified, for example by distillation.

According to the process of the present invention, it is possible to obtain cyclohexyloxyacetic alkyl esters in a purity of more than 99% by weight and a distilled yield of 98%.

According to the process of the present invention, it is possible to prepare cyclohexyloxyacetic alkyl esters in high purity and in very good yield. This means that the process according to the present invention is advantageous, particularly from cost and industrial aspects.

The cyclohexyloxyacetic alkyl esters prepared by the process according to the present invention can be converted to cyclohexyloxyacetic allyl ester.

For the preparation of cyclohexyloxyacetic allyl ester, preference is given to methyl cyclohexyloxyacetate, ethyl cyclohexyloxyacetate, isopropyl cyclohexyloxyacetate, propyl cyclohexyloxyacetate, isobutyl cyclohexyloxyacetate and butyl cyclohexyloxyacetate, and more preference is given to methyl cyclohexyloxyacetate, ethyl cyclohexyloxyacetate and isopropyl cyclohexyloxyacetate.

It has also been found that the cyclohexyloxyacetic alkyl esters have fragrance properties. In particular, the cyclohexyloxyacetic alkyl esters having alkyl radicals containing 1 to 5 carbon atoms have fragrance properties with a fruity, pineapple-like character. Preferred fragrances are cyclohexyloxyacetic alkyl esters having the alkyl radicals R=methyl, ethyl, propyl, isopropyl, butyl, isobutyl, tertiary butyl, pentyl and isopentyl. More preferred fragrances are the cyclohexyloxyacetic alkyl esters with R=methyl, propyl, isopropyl and isopentyl.

The odor description of some cyclohexyloxyacetic alkyl esters in detail:
methyl cyclohexyloxyacetate:
fresh, fruity, lactonic, galbanum-like, herbaceous
ethyl cyclohexyloxyacetate:
fresh, fruity, grapefruit, orange, galbanum-like, herbaceous
isopropyl cyclohexyloxyacetate:
fresh, fruity, aldehydic, green, balsamic, chocolatey
propyl cyclohexyloxyacetate:
fresh, fruity, aldehydic, green
isobutyl cyclohexyloxyacetate:
fresh, fruity, aldehydic, green, chocolatey
butyl cyclohexyloxyacetate:
fresh, aldehydic, green, pineapple-like
isoamyl cyclohexyloxyacetate:
fresh, fruity, aldehydic, green, chocolatey, pineapple-like, galbanum-like
isooctyl cyclohexyloxyacetate:
herbaceous, green In the case of higher cyclohexyloxyacetic alkyl esters, a fatty side-note may arise.

The invention is further illustrated but is not intended to be limited by the following examples in which all parts and percentages are by weight unless otherwise specified.

EXAMPLES

Example 1

2,600 g of methyl phenoxyacetate (GC purify 99.8% by weight) and 40 g of palladium on activated carbon 5% by weight (moist, 40% by weight water content) were initially introduced into a stirred autoclave with gas-dispersion stirrer. Hydrogenation was carried out for 33 hours at 110 to 120° C. and a hydrogen pressure of 20 bar. After filtration, 2,650 g of methyl cyclohexyloxyacetate with a purity of 99.3% by weight were obtained. The resulting methyl cyclohexyloxyacetate could be distilled essentially without residue at a bottoms temperature of 120° C. and 1 mbar. The theoretical yield was 98.4%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of cyclohexyloxyacelic alkyl esters comprising the step of hydrogenating phenoxyacetic alkyl esters in the presence of a catalyst comprising at least one metal from subgroup 8 in elemental form.

2. A process according to claim 1, wherein the catalyst comprises palladium, platinum, ruthenium, and rhodium.

3. A process according to claim 2, wherein the catalyst comprises palladium.

4. A process according to claim 1 wherein the catalyst comprises at least one inorganic support material.

5. A process according to claim 4, wherein the catalyst is palladium on activated carbon.

6. A process according to claim 1, wherein the weight ratio of the amount of metal to phenoxyacetic alkyl ester is in the range 1:100 to 1:10,000.

7. A process according to claim 1, wherein hydrogenation is carried out in the absence of a solvent.

8. A process according to claim 1, wherein the hydrogen pressure is 1 to 100 bar.

9. A fragrance comprising one or more cyclohexyloxyacetic alkyl esters, having alkyl radicals containing 1 to 5 carbon atoms and having a fruity character.

* * * * *